United States Patent
Moritake et al.

(10) Patent No.: US 6,840,673 B2
(45) Date of Patent: Jan. 11, 2005

(54) GANTRY SYSTEM AND X-RAY CT SYSTEM

(75) Inventors: Masahiro Moritake, Tokyo (JP);
Masashi Maida, Tokyo (JP); Katsumi Azu, Tokyo (JP); Daigo Urabe, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 149 days.

(21) Appl. No.: 10/284,671

(22) Filed: Oct. 31, 2002

(65) Prior Publication Data

US 2003/0095635 A1 May 22, 2003

(30) Foreign Application Priority Data

Nov. 19, 2001 (JP) ........................................ 2001-353408

(51) Int. Cl.⁷ ................................................. H05G 1/02
(52) U.S. Cl. ...................................... 378/198; 378/196
(58) Field of Search ............................... 378/4, 17, 20, 378/193, 196, 197, 198

(56) References Cited

U.S. PATENT DOCUMENTS

| | | | |
|---|---|---|---|
| 3,840,221 A | 10/1974 | Hogan | |
| 4,034,224 A | 7/1977 | Heavens et al. | |
| 4,088,888 A | 5/1978 | Brook et al. | |
| 4,131,802 A | 12/1978 | Braden et al. | |
| 4,452,439 A | 6/1984 | Hogan | |
| 4,567,894 A | 2/1986 | Bergman | |
| 4,629,989 A | 12/1986 | Riehl et al. | |
| 4,645,933 A | * 2/1987 | Gambini et al. | 250/363.05 |
| 4,727,328 A | 2/1988 | Carper et al. | |
| 4,928,283 A | * 5/1990 | Gordon | 378/20 |
| 5,600,858 A | 2/1997 | Baer | |
| 5,619,763 A | 4/1997 | Randolph et al. | |
| 6,212,251 B1 | * 4/2001 | Tomura et al. | 378/15 |
| 6,452,999 B1 | 9/2002 | Maida | |
| 6,508,586 B2 | * 1/2003 | Oota | 378/196 |

* cited by examiner

Primary Examiner—David V. Bruce
Assistant Examiner—Courtney Thomas
(74) Attorney, Agent, or Firm—Carl B. Horton, Esq.; Armstrong Teasdale LLP

(57) ABSTRACT

For the purpose of reducing a deviation in the rotational center of scan and a deviation in scan position in the direction of length of a rail, a gantry system including a pair of runway rails and a gantry in an X-ray CT system that can move along the runway rails, is characterized by comprising a linear guide rail arranged in the direction along the runway rails and linear guide blocks mounted on the gantry and slidably fitted on the linear guide rail.

13 Claims, 10 Drawing Sheets

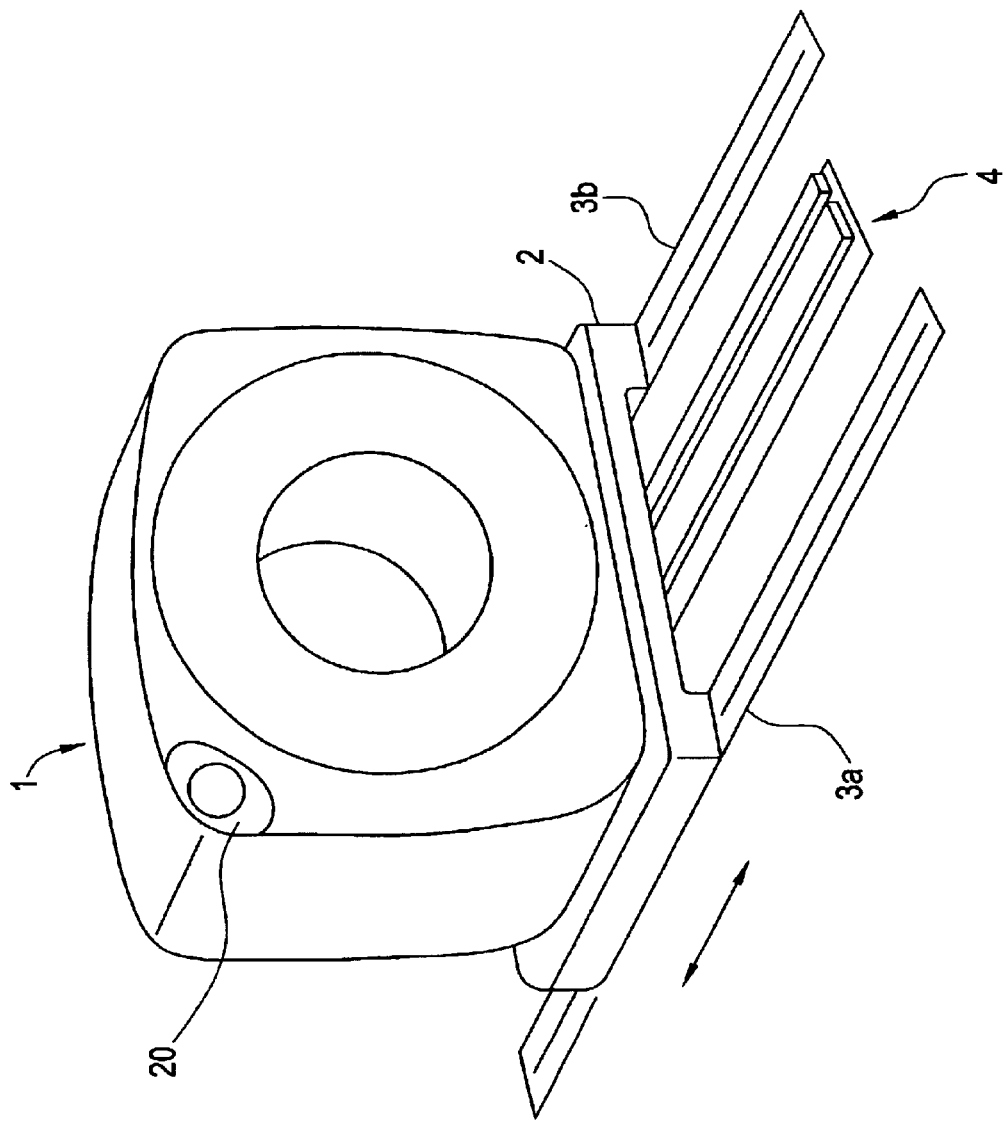
FIG. 1
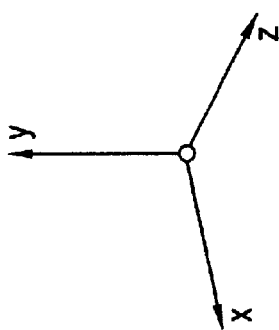

GANTRY SYSTEM AND X-RAY CT SYSTEM

CROSS REFERENCE TO RELATED APPLICATIONS

This application claims the benefit of Japanese Application No. 2001-353408 filed Nov. 19, 2001.

BACKGROUND OF THE INVENTION

The present invention relates to a position control technology of a gantry in an X-ray CT (Computed Tomography) that performs a scan to take a tomogram of an object to be inspected while moving the gantry.

An X-ray CT system has been known whose gantry is mounted on a bogie moving on rails by means of wheels and which performs a scan of an object to be inspected while moving the gantry.

Generally, in a rail, its cross section is formed convexly and the convex portion becomes a rail tread surface. A groove corresponding to the width of the rail tread surface is formed on a wheel tread surface along the direction of rolling of the wheel (that is, the wheel tread surface is formed concavely). This groove is engaged with the rail convex portion to enable the wheel to move along the rail to thereby prevent the wheel from coming off the rail.

In order to roll the wheels on the rails smoothly, a gap of about 0.5 mm to 1 mm is usually provided between the rail tread surface and the groove of the wheel tread surface. Four wheels of the bogie are machined so that they have the same diameter, but there is a little difference in size between them and the difference in size causes the bogie to move not in a straight line but in a little curved line to the left and right side. As the bogie moves forward, the bogie is deviated-in the lateral direction to narrow the provided gap gradually and when one side of the groove comes into contact with one side of the rail, the bogie can not move further in the deviated direction but is moved straight in the direction of length of the rail forcibly by the groove and the rail.

Next, when the bogie moves in the reverse direction, the bogie is deviated reversely in the lateral direction and when the opposite side of the groove comes into contact with the rail, the bogie is forcibly moved straight in the direction of length of the rail. That is, the position of the bogie when the bogie moves forward is deviated in the lateral direction from the position of the bogie when the bogie moves backward. As a result, there is presented a problem that the rotational center of scan rotation is deviated.

Moreover, while an rotary encoder is mounted on the shaft of a driven wheel in the related art to detect the position of the bogie by detecting the rotation of the wheel, as described above, because the position of the bogie when the bogie moves forward is deviated in the lateral direction from the position of the bogie when the bogie moves backward, the wheel does not move in the same locus when the bogie moves forward and when the bogie moves backward. For this reason, there is presented a problem that when the bogie stops at a certain position in the direction of length of the rail, the detection result of position of the bogie is different depending on the direction of movement of the bogie before the stop of the bogie. A problem that a large error is caused in detecting the position of the bogie results in a deviation in a scan position in the direction of length of the rail.

Moreover, the rotation of the rotary encoder depends on the size of the wheel. For this reason, there is also presented a problem that since the detection accuracy of movement distance of the bogie in the direction of length of the rail depends on the machining accuracy of the size of the wheel, a desired position detection accuracy can not be kept.

Further, there is also presented the following problem: while the position of the bogie when the bogie moves back and forth can be recognized by the detection of a limit switch at a retracted position of the gantry, it is necessary for an operator to press a button provided on the gantry to set a zero slice position that is the base of scan (scan base position), which makes operability worse. In particular, this includes a problem that even if changing the scan base position is not required because the predetermined scan base position exists, it is necessary for the operator to input the scan base position manually, which makes operability worse and tends to make an operating miss or to cause a position error.

Still further, safety must be sufficiently secured when the gantry is moved.

SUMMARY OF THE INVENTION

Therefore, it is the object of the present invention to reduce a deviation in the rotational center of scan and a deviation in a scan position in the direction of length of a rail in an X-ray CT system that performs a scan of an object to be inspected while moving a gantry along the rail.

It is another object of the present invention to increase accuracy in detecting the position of a gantry in an X-ray CT system that performs a scan of an object to be inspected while moving the gantry along a rail.

It is still another object of the present invention to improve operability in setting a scan base position in an X-ray CT system that performs a scan of an object to be inspected while moving a gantry along the rail.

It is still another object of the present invention to guarantee safety when a gantry is moved in an X-ray CT system that performs a scan of an object to be inspected while moving a gantry along the rail.

According to the present invention, there is provided a gantry system comprising a pair of runway rails and a gantry in an X-ray CT system that can move along the runway rails, characterized by a linear guide rail arranged in the direction along the runway rails and a linear guide block mounted on the gantry and slidably fitted on the linear guide rail.

Further, according to the present invention, there is also provided an X-ray CT system for performing a scan of an object to be inspected while moving a gantry, comprising: a storage unit for previously storing a distance from a predetermined check point to an initial scan base position in the direction of movement of the gantry; a measurement unit for measuring a position in the direction of movement of the gantry; a detection unit for detecting that the gantry is moved to the check point; and a setting unit for setting a scan base position based on a position measured by the measurement unit when the gantry is moved to the check point and the distance stored in the storage unit.

Still further, according to the present invention, there is provided a method of controlling an X-ray CT system that includes a gantry mounted on a runway rail and movable along the runway rail, a measurement unit for measuring a position in the direction of movement of the gantry, a detection unit for detecting that the gantry is moved to a predetermined check point, and a storage unit for previously storing a distance from the predetermined check point to an initial scan base position in the direction of movement of the gantry, and that performs a scan of a body to be inspected while moving the gantry, the method comprising: a detection step of detecting that the gantry is moved to the predetermined check point by the detection unit; a measurement step of measuring a position when the gantry is moved to the predetermined check point by the measurement unit; and a setting step of setting a scan base position based on a position measured at the measurement step and the distance stored in the storage unit.

Still further, according to the present invention, there is provided a program for controlling an X-ray CT system that includes a gantry mounted on a runway rail and movable along the runway rail, a measurement unit for measuring a position in the direction of movement of the gantry, a detection unit for detecting that the gantry is moved to a predetermined check point, and a storage unit for previously storing a distance from the predetermined check point to an initial scan base position in the direction of movement of the gantry, and that performs a scan of a body to be inspected while moving the gantry, the program comprising the program codes of: a detection step of detecting that the gantry is moved to the predetermined check point by the detection unit; a measurement step of measuring a position when the gantry is moved to the predetermined check point by the measurement unit; and a setting step of setting a scan base position based on a position measured at the measurement step and the distance stored in the storage unit.

Still further, according to the present invention, there is also provided a storage medium storing a program for controlling an X-ray CT system that includes a gantry mounted on a runway rail and movable along the runway rail, a measurement unit for measuring a position in the direction of movement of the gantry, a detection unit for detecting that the gantry is moved to a predetermined check point, and a storage unit for previously storing a distance from the predetermined check point to an initial scan base position in the direction of movement of the gantry, and that performs a scan of a body to be inspected while moving the gantry, the storage medium storing the program codes of: a detection step of detecting that the gantry is moved to the predetermined check point by the detection unit; a measurement step of measuring a position when the gantry is moved to the predetermined check point by the measurement unit; and a setting step of setting a scan base position based on a position measured at the measuring step and the distance stored in the storage unit.

Still further, according to the present invention, there is provided a method of controlling an X-ray CT system that includes a gantry mounted on a runway rail and movable along the runway rail, a measurement unit for measuring a position in the direction of movement of the gantry, a detection unit for detecting that the gantry is moved to predetermined first and second check points, and a storage unit for previously storing a first distance to show a distance from the first check point to the second check point and a second distance to show a distance from the second check point to an initial scan base position, in the direction of movement of the gantry, and that performs a scan of an object to be inspected while moving the gantry, the method comprising: a first detection step of detecting that the gantry is moved to the first check point by the detection unit; a first measurement step of measuring a position when the gantry is moved to the first check point by the measurement unit; a second detection step of detecting that the gantry is moved to the second check point by the detection unit; a second measurement step of measuring a position when the gantry is moved to the second check point by the measurement unit; and a setting step of setting a scan base position based on a position measured at the second measurement step and the second distance stored in the storage unit.

Still further, according to the present invention, there is provided a program for controlling an X-ray CT system that includes a gantry mounted on a runway rail and movable along the runway rail, a measurement unit for measuring a position in the direction of movement of the gantry, a detection unit for detecting that the gantry is moved to predetermined first and second check points, and a storage unit for previously storing a first distance to show a distance from the first check point to the second check point and a second distance to show a distance from the second check point to an initial scan base position, in the direction of movement of the gantry, and that performs a scan of an object to be inspected while moving the gantry, the program comprising the program codes of: a first detection step of detecting that the gantry is moved to the first check point by the detection unit; a first measurement step of measuring a position when the gantry is moved to the first check point by the measurement unit; a second detection step of detecting that the gantry is moved to the second check point by the detection unit; a second measurement step of measuring a position when the gantry is moved to the second check point by the measurement unit; and a setting step of setting a scan base position based on a position measured at the second measurement step and the second distance stored in the storage unit.

Still further, according to the present invention, there is also provided a storage medium storing a program for controlling an X-ray CT system that includes a gantry mounted on a runway rail and movable along the runway rail, a measurement unit for measuring a position in the direction of movement of the gantry, a detection unit for detecting that the gantry is moved to predetermined first and second check points, and a storage unit for previously storing a first distance to show a distance from the first check point to the second check point and a second distance to show a distance from the second check point to an initial scan base position, in the direction of movement of the gantry, and that performs a scan of an object to be inspected while moving the gantry, the storage medium storing the program codes of: a first detection step of detecting that the gantry is moved to the first check point by the detection unit; a first measurement step of measuring a position when the gantry is moved to the first check point by the measurement unit; a second detection step of detecting that the gantry is moved to the second check point by the detection unit; a second measurement step of measuring a position when the gantry is moved to the second check point by the measurement unit; and a setting step of setting a scan base position based on a position measured at the second measurement step and the second distance stored in the storage unit.

Still further, according to the present invention, there is also provided an X-ray CT system that includes a gantry mounted on a runway rail and movable along the runway rail and an operating console connected to the gantry and outputting information relating to scan to the gantry and performs a scan of an body to be inspected while moving the gantry, comprising: a first direction unit that is mounted on the gantry and directs the gantry to move; a second direction unit that is mounted on the operating console and directs the gantry to move; a storage unit that stores information of a maximum range in which the gantry is moved by the first direction unit; and a control unit that controls the movable range of the gantry by the second direction unit in accordance with the maximum range in which the gantry is moved by the first direction unit.

According to the present invention, in an X-ray CT system that performs a scan of a body to be inspected while moving a gantry along rails, it is possible to reduce a deviation in the rotational center of scan and a deviation in scan position in the direction of length of the rail.

Further, according to the present invention, in an X-ray CT system that performs a scan of a body to be inspected while moving a gantry along rails, it is possible to increase the accuracy of detecting the position of the gantry.

Still further, according to the present invention, in an X-ray CT system that performs a scan of a body to be inspected while moving a gantry along rails, it is possible to improve operability in setting the scan base position.

Still further, according to the present invention, in an X-ray CT system that performs a scan of a body to be inspected while moving a gantry along rails, it is possible to ensure safety when the gantry is moved.

Further objects and advantages of the present invention will be apparent from the following description of the preferred embodiments of the invention as illustrated in the accompanying drawings.

BRIEF DESCRIPTION OF DRAWINGS

FIG. 1 is an external perspective view to show one example of a gantry mounted on rails in an embodiment.

DETAILED DESCRIPTION OF THE INVENTION

Modes for carrying out the invention will be described in detail with reference to the drawings.

FIG. 1 is a schematic perspective view to show one example of a gantry in an X-ray CT system mounted on rails in a mode for carrying out the invention.

As shown in FIG. 1, a gantry 1 has a gantry base part 2 and is mounted on a pair of side rails 3a and 3b. The gantry 1 can move along the side rails 3a, 3b and while the gantry 1 moves, a scan is performed. Moreover, a center rail 4 is disposed at the central position sandwiched between the side rails 3a and 3b in the direction along the side rails 3a and 3b. The structure of the center rail 4 will be described later.

For the sake of convenience in the following description, let's define a direction of disposition of the side rails 3a and 3b, that is, a direction in which the gantry moves, as a z-axis direction, a direction along a floor and perpendicular to the z-axis direction as an x-axis direction, and a direction perpendicular to the floor (vertical direction) as a y-axis direction.

Figure 2:
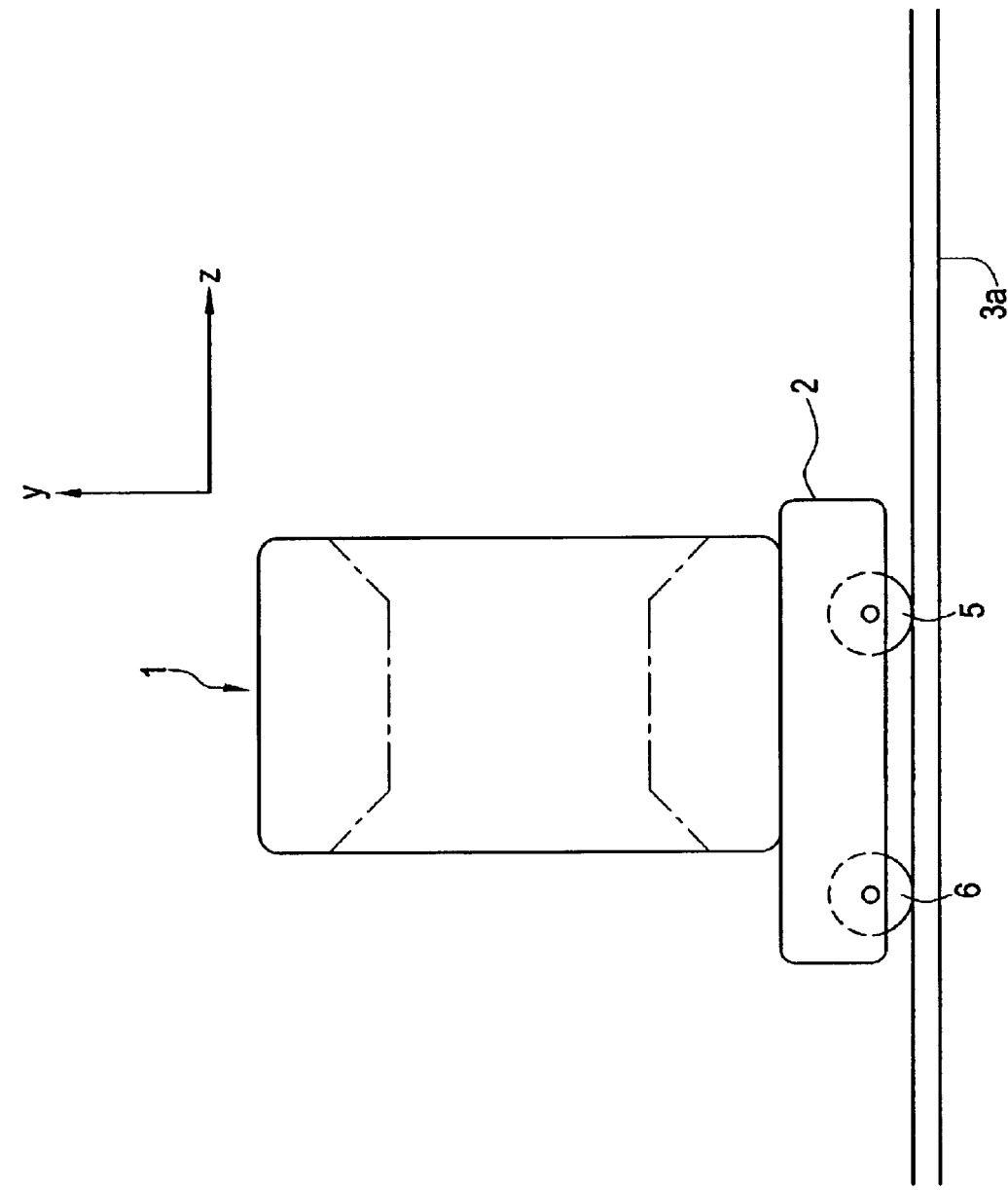
FIG. 2 is a side view of the gantry in the embodiment.

FIG. 2 is a side view of the gantry 1 shown in FIG. 1. As shown in FIG. 1, wheels rolling on the side rails are provided in the gantry base part 2 (wheels 5, 6 rolling on the side rail 3a are shown in FIG. 2). This enables the gantry 1 to move in the z-axis direction.

Figure 3:
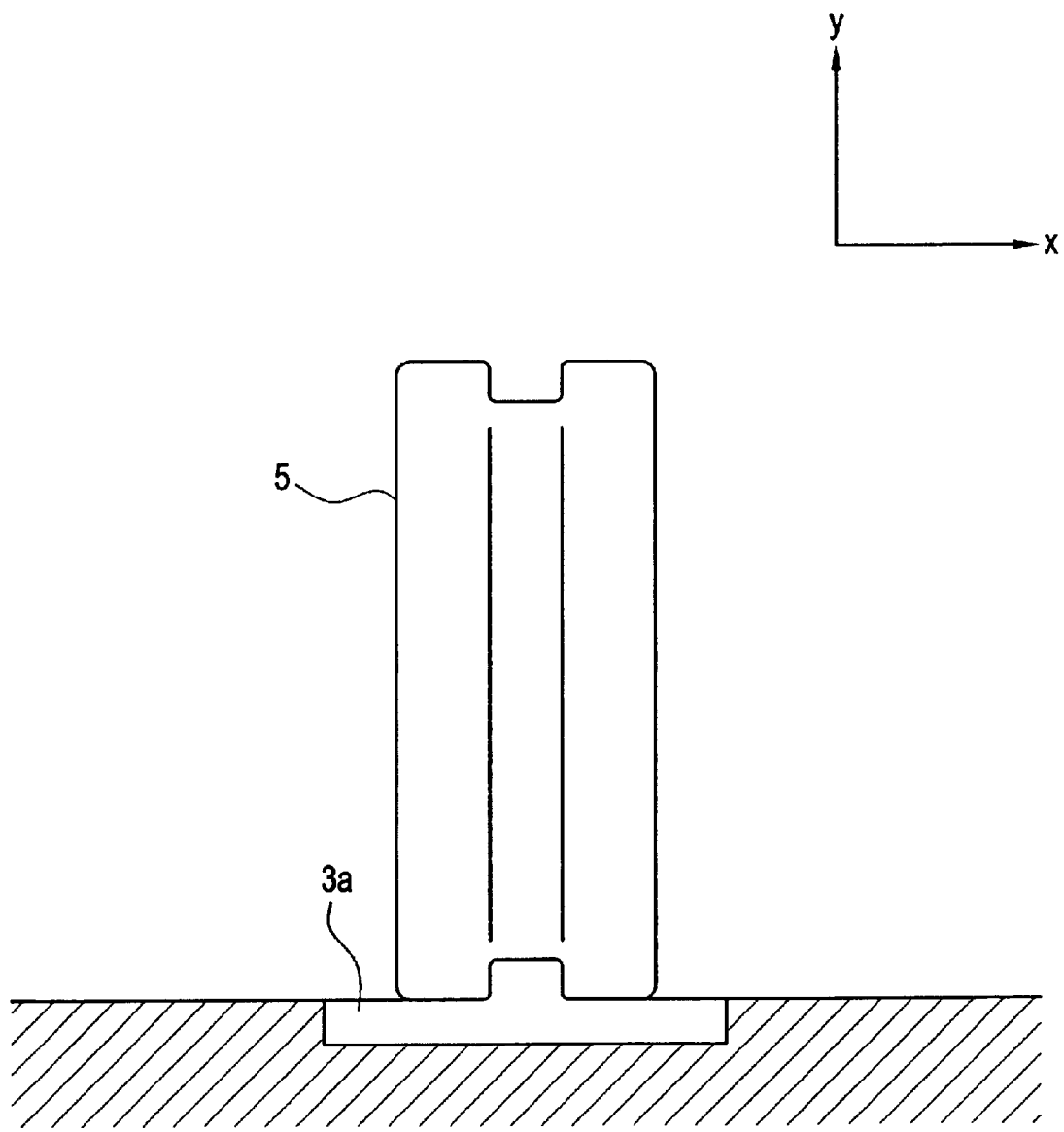
FIG. 3 is an illustration to show the relationship between wheel and side rail in the embodiment.

FIG. 3 is an illustration to show the relationship between the wheel 5 and the side rail 3a. As shown in FIG. 3, the side rail 3a is formed convexly in its cross section and its protruding portion becomes a rail tread surface. Moreover, a groove corresponding to the width of the rail tread surface is formed on the wheel tread surface of the wheel 5 along the direction in which the wheel rolls. That is, the wheel tread surface is formed concavely. Then, the groove is engaged with the rail's protruding portion to enable the wheel 5 to move along the rail 3a to thereby prevent the wheel from coming off the rail. This holds true also for the other wheels.

Figure 4:
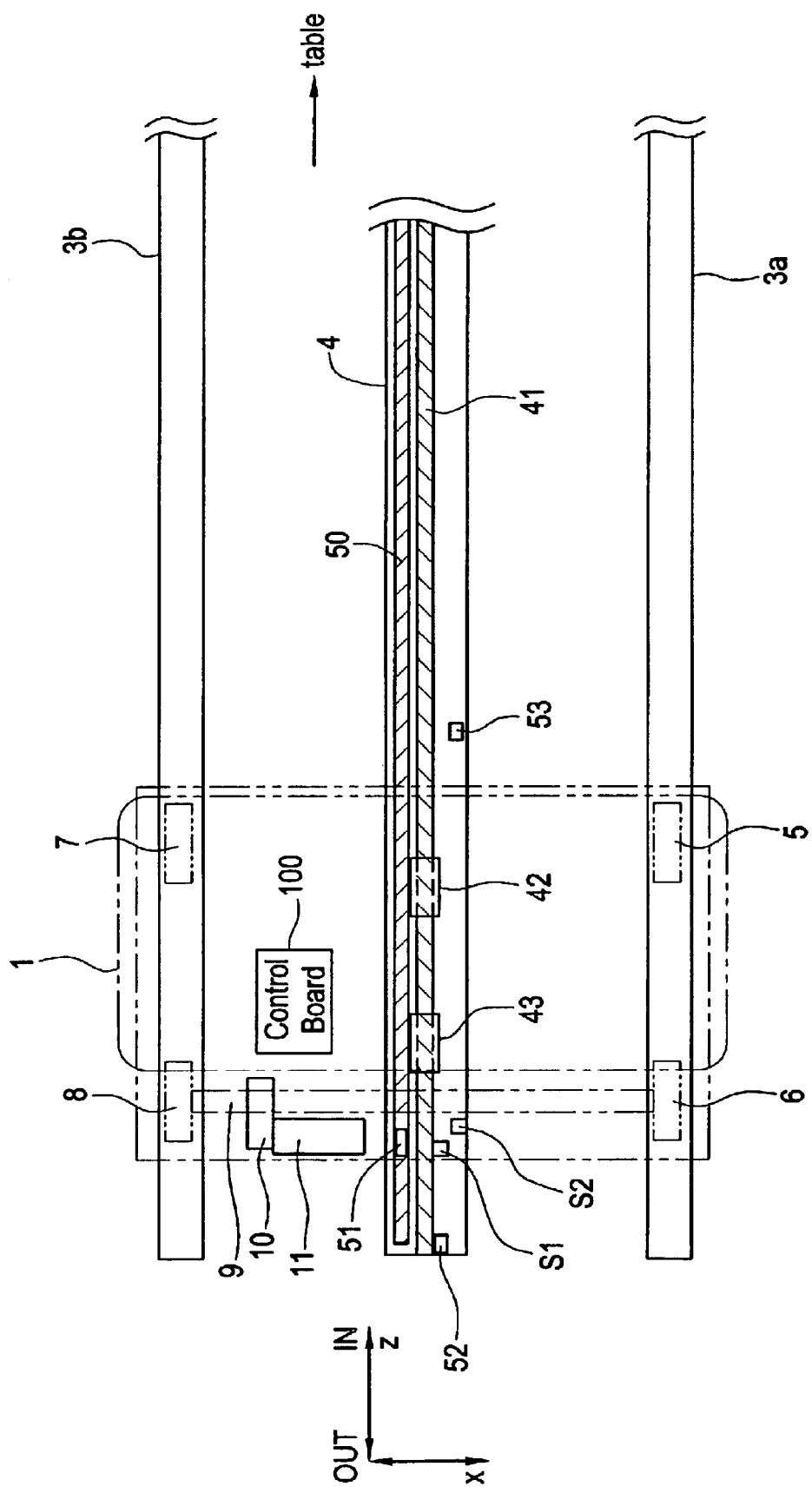
FIG. 4 is a top perspective view of side rails, a center rail, and the gantry.

FIG. 4 is a top perspective view to show the side rails 3a and 3b, the center rail 4, and the gantry 1 which are shown in FIG. 1.

As described above, the wheels 5, 6 are set on the side rail 3a whereas wheels 7, 8 are set on the other side rail 3b. The wheels 6 and 8 are connected to each other by a shaft 9 and are driven by a motor 11 via a gear 10 (both of them are mounted in the gantry base part 2). That is, the wheels 6, 8 are driving wheels and the wheels 5, 7 are driven wheels.

Figure 5:
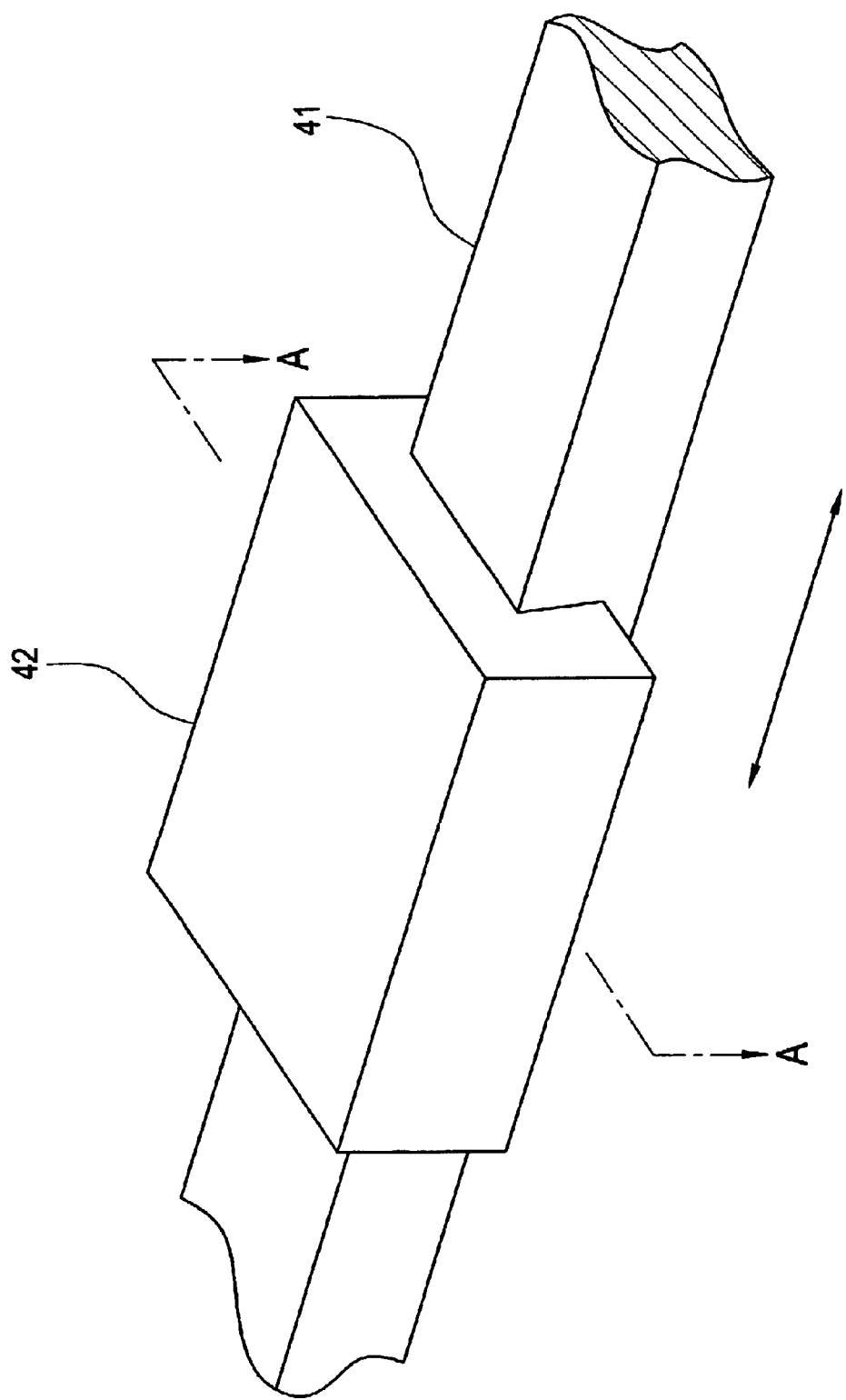
FIG. 5 is an illustration to show one example of a state where a linear guide block is mounted on a linear guide rail.
Figure 6:
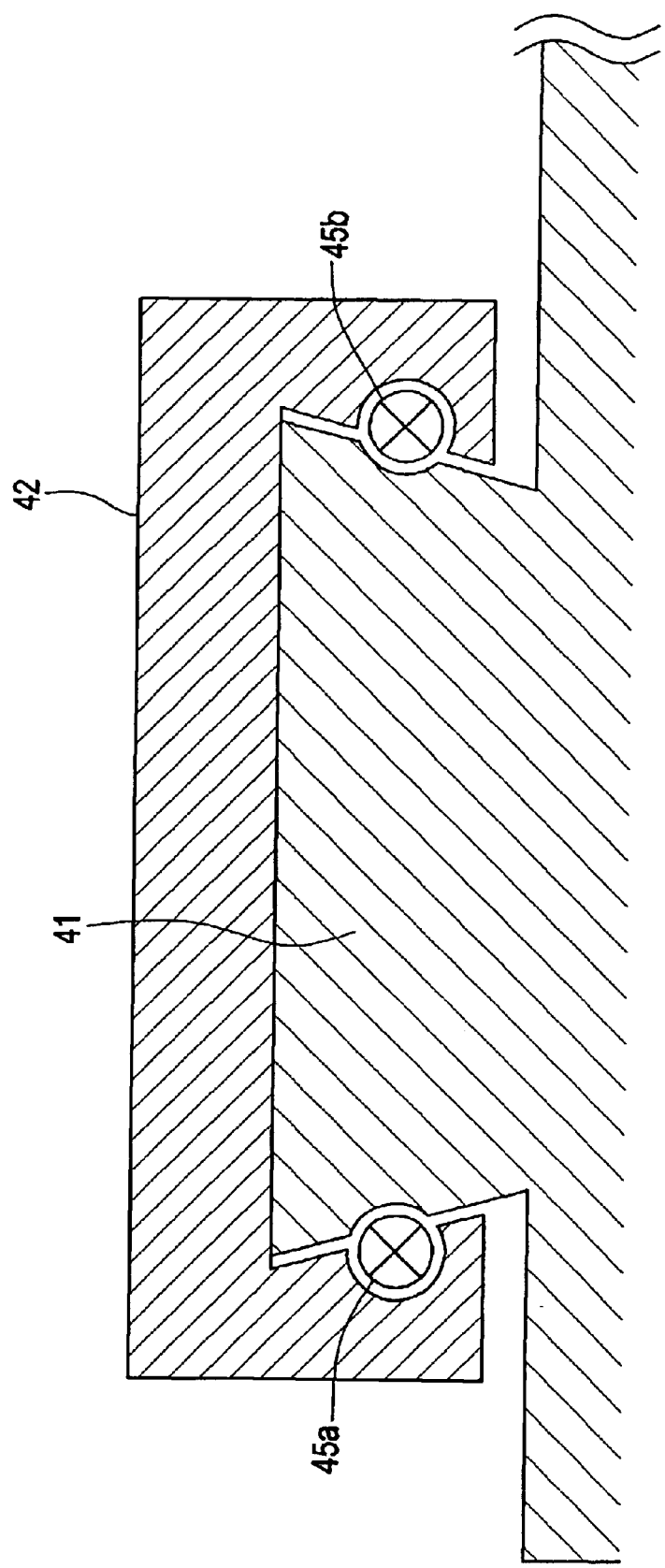
FIG. 6 is a cross-sectional view taken on a line A—A in FIG. 5.

A linear guide rail 41 is mounted on the center rail 4 in the z-axis direction. Then, two linear guide blocks 42, 43 mounted on the bottom surface of the gantry base part 2 are mounted on the linear guide rail 41 so that they can slide on the linear guide rail 41. FIG. 5 shows one example of a state in which the linear block 42 is mounted on the linear guide rail 41 and FIG. 6 shows a cross-sectional view taken on a line A—A in FIG. 5. Referring to this cross-sectional view makes it clear that the linear guide block 42 is fitted on the linear guide rail 41 with bearings 45a, 45b interposed between their side surfaces. Such structure enables the linear guide block 42 to slide along the linear guide rail 41. This holds true also for the linear guide block 43.

Moreover, in order to absorb errors in height of the side rails 3a, 3b and the center rail 4, respectively, the linear guide block 42 is mounted on the bottom surface of the gantry base part 2 with a gap of about several millimeters in the y-axis direction so that it can slide thereon.

Measuring the position of the gantry 1 in the z-axis direction (also simply referred to as a position detection) in the embodiment is performed by the use of a linear encoder. First, a linear scale 50 of the linear encoder is mounted on the center rail 4 along the linear guide rail 41. Further, a pickup sensor 51 is mounted on the gantry base part 2 so as to oppose the linear scale 50. The outputs of this pickup sensor 51 (A-phase and B-phase encoder signals) are sent to a control board 100 (see FIG. 4) and the position of the gantry 1 in the z-axis direction can be measured based on this outputs.

Since the two linear guide blocks 42, 43 mounted on the bottom surface of the gantry base part 2 are fitted in this manner on the linear guide rail 41 mounted on the center rail 4 so that they can freely slide, the deviation of the gantry 1 in the x-axis direction with respect to the movement of the gantry 1 in the z-axis direction is forcibly limited. Therefore, even if the gaps between the grooves of the wheels 5, 6, 7, 8 and the rails 3a, 3b apply forces to the gantry 1 in the x-axis direction as the gantry 1 moves or apply a force for changing the direction of the gantry 1 gradually to the gantry 1 as the gantry 1 moves, the gantry 1 is not deviated by the forces but can be moved correctly straight.

This can reduce a deviation in the rotational center of scan and a deviation in a scan position in the z-axis direction.

Further, it is possible to detect the position of the gantry 1 in the z-axis direction with high accuracy without being affected by the machining accuracy such as the size of the wheel and the direction of an axle. Moreover, since the linear scale 50 is mounted on a lower portion near the center in the x-direction of the gantry 1, even if a force of torsion is applied to the gantry base part 2 to deform the gantry base part 2, it is possible to detect the scan position correctly.

Next, an operation of moving the gantry 1 will be described. Here, referring to FIG. 4, on the right side of paper is provided a table (not shown) on which a body to be inspected is placed. In the following description, in the direction of movement of the gantry 1, that is, in the z-axis direction, let's call a direction in which the gantry is brought near to the table as an IN side and a direction in which the gantry is brought away from the table as an OUT side.

Further, in FIG. 4, on the bottom surface of the gantry base part 2 are mounted a first limit switch S1 and a second limit switch S2. Moreover, a protrusion 52 for operating the first limit switch S1 is provided on an outside movement limit position (OUT limit position) as a first check point on the center rail 4 and a protrusion 53 for operating the second limit switch S2 is provided on a predetermined position sandwiched between the protrusion 52 and the table as a second check point on the center rail 4. These protrusions 52, 53 are used in a processing of setting the scan base position that will be described later.

Figure 7:
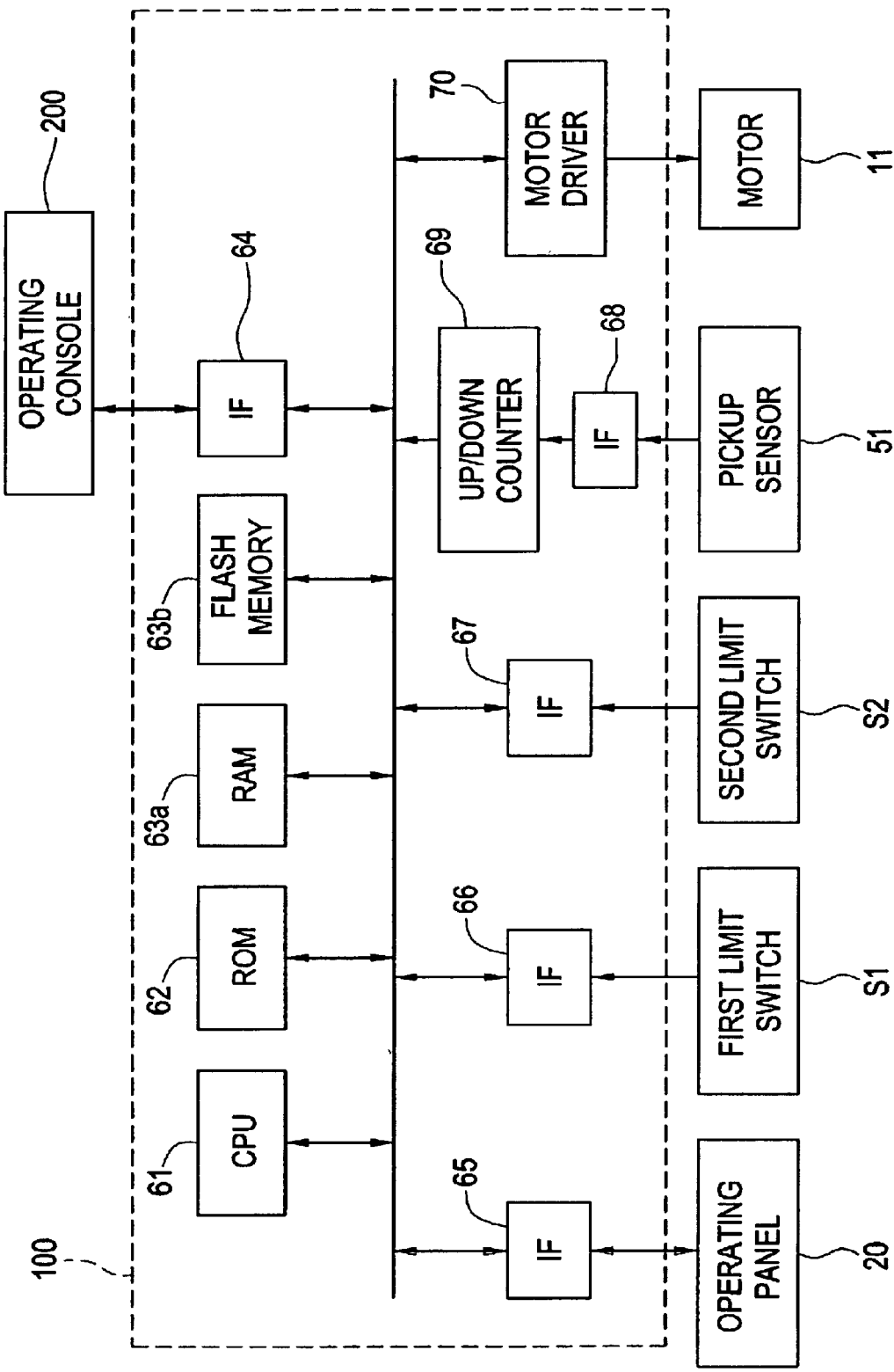
FIG. 7 is a block diagram to show the constitution of a control board built in a gantry base part in the embodiment.

FIG. 7 is a block diagram to show the constitution of the control board 100 (see FIG. 4) built in the gantry base part 2.

In FIG. 7, a reference numeral 61 denotes a CPU for controlling the movement of the gantry 1 and a reference numeral 62 denotes a ROM for storing the operation processing procedure (program) of the CPU 61 and a reference character 63a denotes a RAM functioning as a main storage and a reference character 63b denotes a flash memory functioning as an auxiliary storage. A reference numeral 64 denotes an interface for inputting data from an operator console 200 for outputting information relating to scan to the gantry 1. Reference numerals from 65 to 68 denote a plurality of interfaces for inputting data from an operating panel 20, the first limit switch S1, the second limit switch S2, and the pickup sensor 51. A reference numeral 69 denotes an up/down counter indicating a relative position in the z-axis direction based on the A-phase and B-phase encoder signals from the pickup sensor 51 and a reference numeral 70 denotes a motor driver for performing the driving control of the motor 11.

Before performing a scan, for example, after turning on the power, an operation of moving the gantry 1 once on the IN side and the OUT side by a manual operation to make a check that moving the gantry 1 does not cause a danger is performed. The movement of the gantry 1 by this manual operation can be performed by the use of a movement button provided on the operating panel 20 (see FIG. 1) arranged on the gantry 1.

Figure 8:
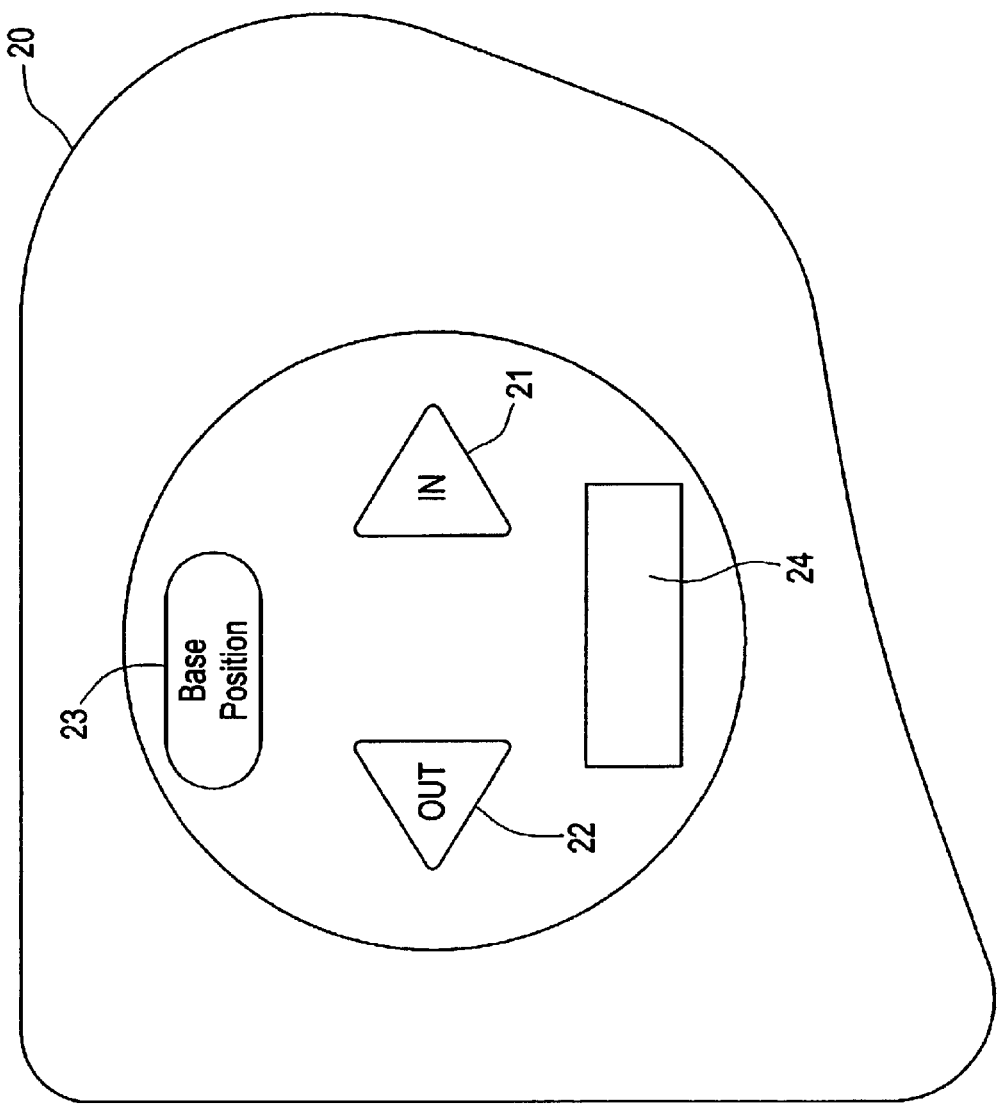
FIG. 8 is an illustration to show one example of an operating panel in the embodiment.

FIG. 8 shows one example of the operating panel 20. A reference numeral 21 denotes a first movement button for moving the gantry 1 on the IN side, and a reference numeral 22 denotes a second movement button for moving the gantry 1 on the OUT side, and a reference numeral 23 denotes a setting button for setting the base position of the scan. Moreover, a reference numeral 24 denotes a display part for producing various displays. Of course, buttons for other objects can be provided but only the ones necessary for describing the present invention are shown in the drawing.

While the operator presses the first movement button 21 (ON), the gantry 1 is moved on the IN side at a predetermined speed. While the operator presses the second movement button 22 (ON), conversely, the gantry 1 is moved on the OUT side at a predetermined speed. In both the buttons, when the operator presses off the button, the button is immediately turned off to stop the movement of the gantry 1.

The maximum range of movement of the gantry 1 performed by this manual operation is stored in the RAM 63a. Then, the gantry 1 can be moved by a remote control from the operating console 200 and in this case, the gantry 1 is allowed to move only within the maximum movement range stored in the RAM 63a.

Here, for example, it is also possible to clear the maximum movement range stored in the RAM 63a when any one of operations of moving the gantry 1 to a retracted position (OUT-side movement limit position), moving the table, and a predetermined operation on the operating console 200 is performed. However, in order to move the gantry 1 or to perform a scan by a remote control thereafter, it is necessary to move the gantry 1 again by the manual operation to make a check of safety.

It is possible to ensure safety by limiting the movable range of the gantry 1 by the remote control in this manner.

Next, a processing of setting the scan base position in the embodiment will be described.

The scan base position can be set by moving the gantry 1 and pressing the setting button 23 at a desired position. As described above, however, there is presented the problem that even if the scan base position is the same for each scan, the setting operation by the setting button 23 (manual setting operation) needs to be performed every time, which makes operability worse. In the case where the manual setting operation is performed every time, a setting error or a setting miss may be caused.

Thus, in the embodiment, the scan base position is automatically set as far as no abnormality is found in the above-described checking operation performed by moving the gantry 1 by the manual operation after turning on the power.

A processing of setting the scan base position in the embodiment will be described in detail by the use of a flow chart shown in FIG. 9 and FIG. 10.

Figure 9:
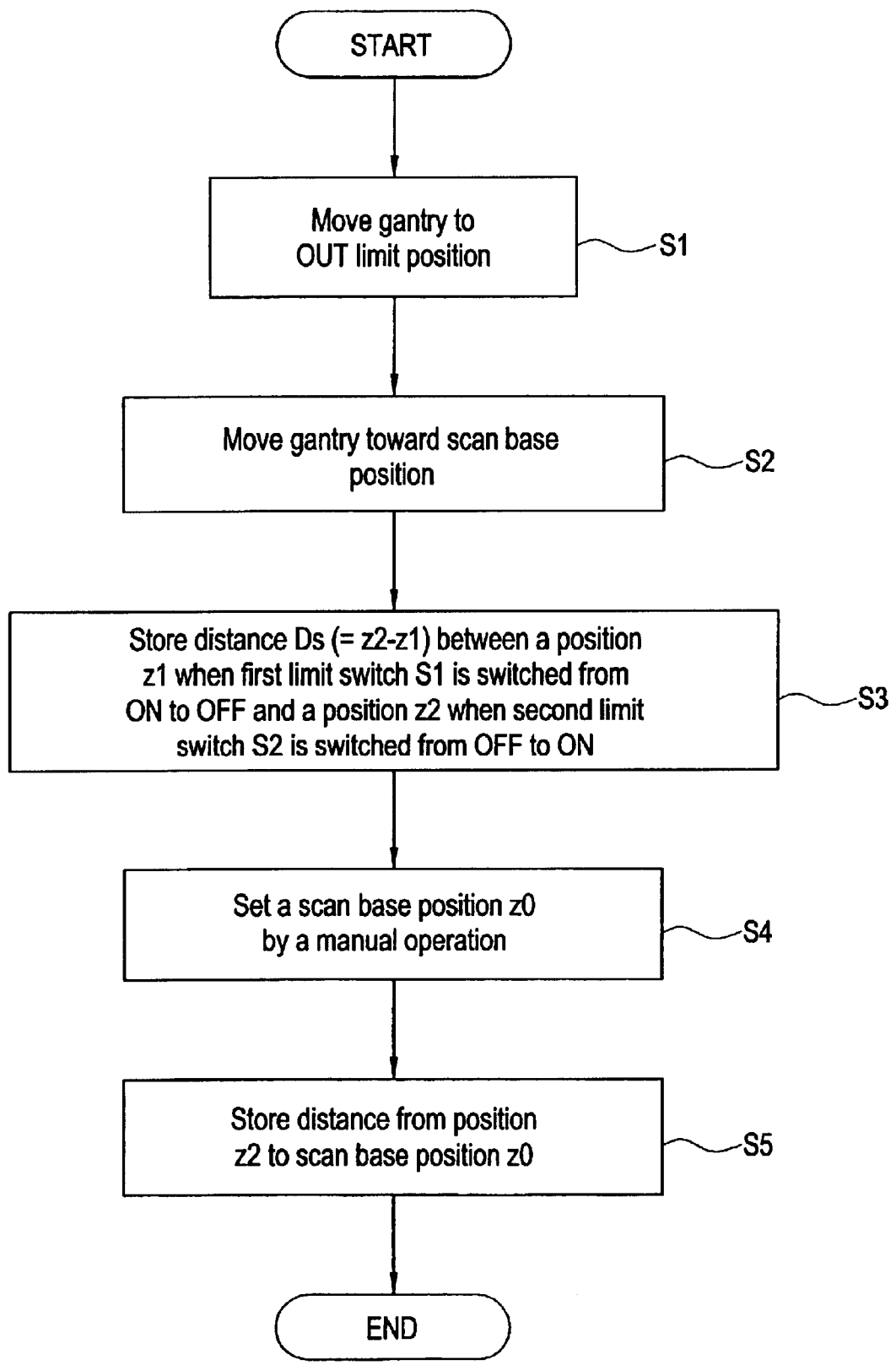
FIG. 9 is a flow chart to show a process of initially setting the positional relations of a first limit switch, a second limit switch, and a desired scan base position, respectively.

FIG. 9 is a flow chart to show a process for setting the positional relations of the first limit switch S1, the second limit switch S2, and the desired scan base position, respectively. It is preferable to perform this process when the system is adjusted. Further, the above-mentioned desired scan base position is usually determined in accordance with the installation environment of the system (such as size of a room).

First, the operator keeps pressing the second movement button 22 to move the gantry 1 to the OUT limit position (step S1). The fact that the gantry is moved to the OUT limit position can be detected by the fact that the first limit switch S1 is put into contact with the protrusion 52 to be switched from OFF to ON. At this time, the gantry is forcibly stopped.

Next, the operator presses the first movement button 21 to move the gantry 1 toward the desired scan base position (step S2). During the movement of the gantry 1, a position z1 where the first limit switch S1 is switched from ON to OFF (first check point) is detected and further a position z2 where the second limit switch S2 is put into contact with the protrusion 53 to be switched from OFF to ON (second check point) is detected, and the distance Ds between z1 and z2 is stored in the flash memory 63b (step S3)

Thereafter, when the gantry 1 comes to a desired position as the scan base position, by the manual operation, that is, by setting the setting button 23, the desired position z0 is set as the scan base position (step S4).

Then, the distance Dr between the position z2 where the second limit switch S2 is switched from OFF to ON and z0 is stored in the flash memory 63b (step S5).

In this manner is finished the process for initially setting the positional relations of the first limit switch S1, the second limit switch S2, the desired scan base position, respectively, which is preferably performed when the system is adjusted.

Figure 10:
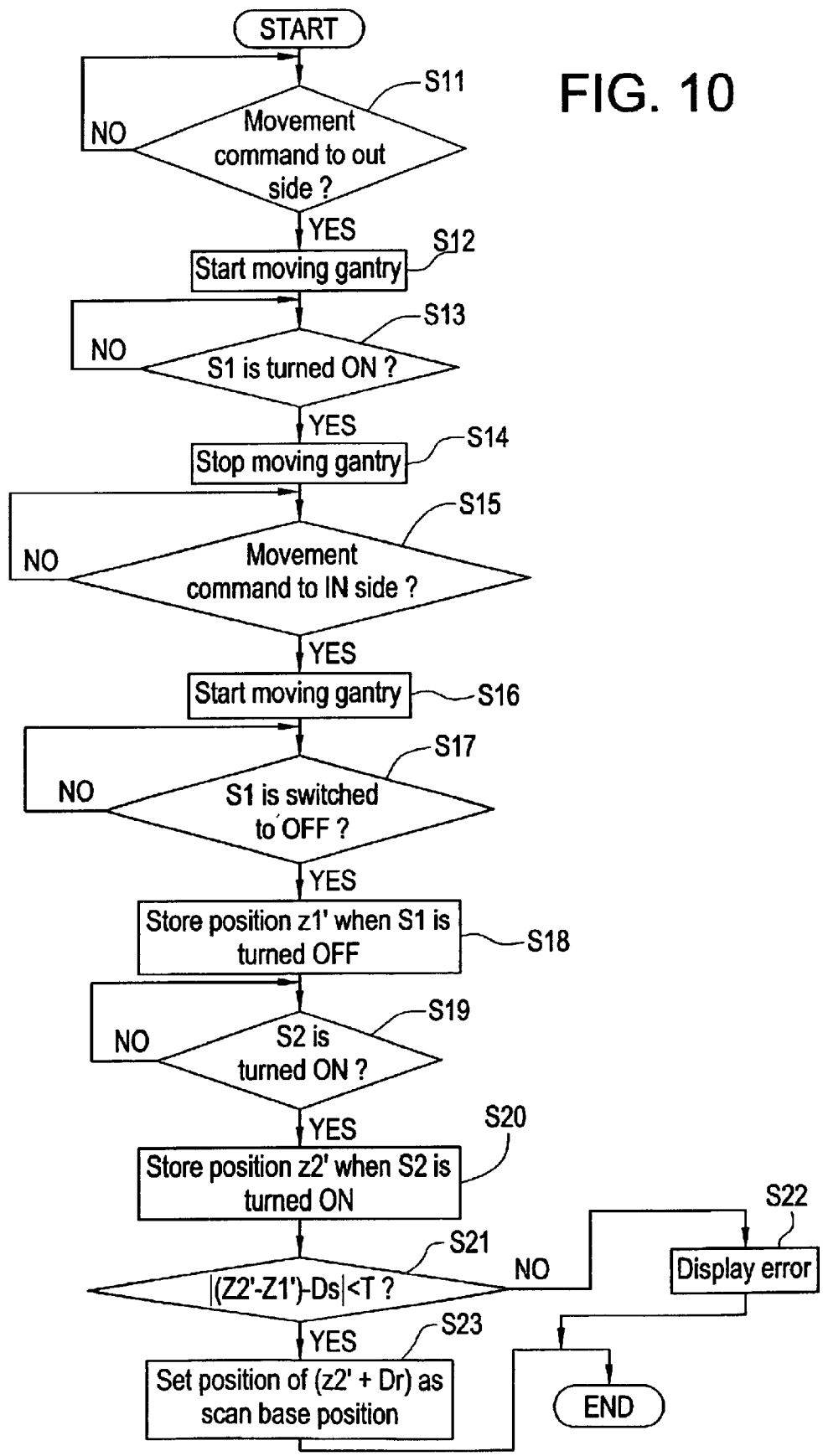
FIG. 10 is a flow chart to show a processing of setting a scan base position in the embodiment.

FIG. 10 is a flow chart to show a processing of setting the scan base position which is performed in a checking operation performed by moving the gantry 1 by the manual operation after turning on the power or the like. A program corresponding to this flow chart is stored in the ROM 62 and is executed by the CPU 61 after turning on the power.

First, at step S11, it is judged based on the input of the second movement button 22 whether a movement command to the OUT side is given or not. When the second movement button 22 is pressed down, the routine advances to step S12 and the gantry 1 starts to move to the OUT side. Here, in the case where the second movement button 22 is separated from the operator to be turned off, at this time, the present process is finished.

At step S13, it is monitored whether the first limit switch S1 is turned ON or not during the movement of the gantry 1. Then, when the first limit switch S1 is turned ON, the routine advances to step S14 where the movement of the gantry 1 is stopped.

Next, at step S15, it is judged based on the input of the first movement button 21 whether a movement command to the IN side is given or not. When the first movement button 21 is pressed down, the routine advances to step S16 and the gantry 1 starts to move to the IN side. Here, also in the case where the first movement button 21 is separated from the operator to be turned off, at this time, the present process is finished.

At step S17, it is monitored whether the first limit switch S1 is switched from ON to OFF or not. Then, when the first limit switch S1 is turned OFF, at step S18, a position Z1' at this time is stored in the RAM 63a.

Next, at step S19, it is monitored whether or not the second limit switch S2 is switched from OFF to ON during the movement of the gantry 1. Then, when the second limit switch S2 is turned ON, at step S20, a position z2' at this time is stored in the RAM 63a.

Next, at step S21, it is judged whether or not the error between the distance between the position z1' when the first limit switch S1 is switched from ON to OFF and the position z2' when the second limit switch S2 is switched from OFF to ON and the distance information Ds stored in the flash memory 63b is within a predetermined range.

That is, it is judged whether or not the error satisfies the following equation.

$$|(z2'-z1')-Ds|<T$$

where T designates a predetermined threshold value.

Here, in the case where the above-mentioned equation is not satisfied, a position detection by any one of the first limit switch S1, the second limit switch S2, and the pickup sensor 51 is judged to be not correct and the routine advances to step S22 where a predetermined error is displayed on the display part 24, or an alarm sound may be issued to inform the operator of an error. In any case, in the case of such error, the scan in this state is prohibited.

Further, in the case where the above-mentioned equation is satisfied, the routine advances to step S23 where a position obtained by adding the distance information Dr stored in the flash memory 63b to the position z2' when the second limit switch S2 is switched from OFF to ON is set as the scan base position and where the obtained base position information is stored in the RAM 63a.

In the case where the base position in each scan is the same, as far as no abnormality is found in the checking operation performed by moving the gantry 1 by the manual operation performed after turning on the power, the scan base position is automatically set, so that operability can be drastically improved and the occurrence of a setting error and a setting miss can be prevented.

Further, in the case where an abnormality is caused in a position detection mechanism provided in the system, the abnormality is informed and the scan in this state is prohibited, so that safety can be ensured.

Here, while the protrusions 52, 53 are provided at the predetermined positions in the direction of movement of the gantry 1 and the predetermined positions are detected by the use of the limit switches S1, S2 that are operated when they come in contact with the protrusions 52, 53 in the embodiment described above, the predetermined positions can be detected also by the other means, for example, a combination of an optical sensor and an optical passing slit, a combination of an optical sensor and an optical reflector, a magnetic position detection sensor, a position detection sensor by an electrostatic capacity, a position detection by an image by means of a CCD camera, and the like.

Further, while the OUT limit position is made the first check point and a position where the gantry 1 is moved forward by a predetermined distance from the first check point is made the second check point in the embodiment described above, it is also recommended that a sensor for detecting the first check point and a sensor for detecting the second check point are provided independently from each other and that the first check point and the second check point be provided at the positions that are detected by both the sensors at the same time when the gantry 1 is moved to the predetermined position.

Further, at step S5 in FIG. 9, the distance Dr from the second check point z2 to the scan base position z0 by the manual operation is stored, and at step S5 in FIG. 10, the scan base position is set again by using this Dr, but it is also recommended that the distance Dr' from the first check point z1 to the scan base position z0 by the manual operation be stored at step S5 in FIG. 9 and that the scan base position be set again by using this Dr' at step S23 in FIG. 10.

Still further, while two linear guide blocks 42, 43 mounted on the bottom surface of the gantry base part 2 are mounted on the linear guide rail 41 in the embodiment described above, as far as they are fixed with sufficient accuracy so that the direction of the gantry 1 is not changed, it is also recommended that only one guide block be used.

Many widely different embodiments of the invention may be configured without departing from the spirit and the scope of the present invention. It should be understood that the present invention is not limited to the specific embodiments described in the specification, except as defined in the appended claims.

What is claimed is:

1. A gantry system comprising a pair of runway rails and a gantry in an X-ray CT system that can move along the runway rails, further comprising a linear guide rail arranged between the runway rails and in the direction along the runway rails and a linear guide block mounted on the gantry and slidably fitted on the linear guide rail via a plurality of bearings located between a surface of the linear guide block and a surface of the linear guide rail.

2. The gantry system of claim 1, wherein the linear guide rail is arranged nearly at a central position of the pair of runway rails.

3. The gantry system of claim 1, further comprising a linear encoder for including a linear scale and a pickup sensor, and configured to measure a position in the direction of movement of the gantry, wherein the linear scale of the linear encoder is arranged along the direction of movement of the gantry, and wherein the pickup sensor of the linear encoder is mounted on the gantry in such a way as to oppose the linear scale.

4. The gantry system of claim 1, further comprising a linear scale nearly at a central position of the pair of runway rails.

5. The gantry system of claim 1, further comprising: a storage unit for storing a distance from a position of a predetermined check point to an initial scan base position in the direction of movement of the gantry; a detection unit for detecting that the gantry moves to the predetermined check point; a linear encoder configured to measure the position of the predetermined check point; and a setting unit for setting a scan base position based on a position measured by the linear encoder when the gantry is moved to the predetermined check point and the distance stored in the storage unit.

6. The gantry system of claim 1, further comprising:
a storage unit configured to store a position of a predetermined check point and to store an initial scan base position in a direction of movement of the gantry, wherein the predetermined check point includes a first check point and a second check point positioned between the first check point and the initial scan base position, wherein the storage unit previously stores a first distance from the first check point to the second check point and a second distance from the second check point to the initial scan base position;
a detection unit including a first sensor for detecting that the gantry is moved to the first check point and a second sensor for detecting that the gantry is moved to the second check point;
a linear encoder configured to measure the position of the predetermined check point;
a setting unit configured to set a scan base position based on a position measured by the linear encoder when the gantry is moved to the second check point and the second distance stored in the storage unit.

7. The gantry system of claim 1, further comprising;
a storage unit configured to store a first distance and a second distance, wherein the first distance is measured between a first gantry position checkpoint and a second gantry position checkpoint;
a judgment unit for judging whether or not an error between the first distance and the second distance stored in the storage unit is within a predetermined range;and
an informing unit for informing a judgment result of the judgment unit in accordance with the judgment result.

8. An X-ray CT system for performing a scan of an object to be inspected while moving a gantry, comprising:
a storage unit for previously storing a distance from a predetermined check point to an initial scan base position in a direction of movement of the gantry;
a measurement unit for measuring a position in the direction of movement of the gantry;
a detection unit for detecting that the gantry is moved to the check point; and
a setting unit for setting a scan base position based on a position measured by the measurement unit when the gantry is moved to the check point and the distance stored in the storage unit.

9. The X-ray CT system of claim 8, further comprising a linear encoder configured to measure the position of the predetermined check point, wherein the predetermined check point includes a first check point and a second check point positioned between the first check point and the initial scan base position, wherein the storage unit stores a first distance to show a distance from the first check point to the second check point and a second distance to show a distance from the second check point to the initial scan base position, wherein the detection unit includes a first sensor for detecting that the gantry is moved to the first check point and a second sensor for detecting that the gantry is moved to the second check point, and wherein the setting unit sets a scan base position based on a position measured by the linear encoder when the gantry is moved to the second check point and the second distance stored in the storage unit.

10. The X-ray CT system of claim 9, further comprising a judgment unit for judging whether or not an error between a distance between a position measured when the gantry is moved to the first check point and a position measured when the gantry is moved to the second check point and the first distance stored in the storage unit is within a predetermined range, and an informing unit for informing a judgment result of the judgment unit in accordance with the judgment result.

11. An X-ray CT system that includes a gantry mounted on a runway rail and movable along the runway rail and an operating console connected to the gantry and configured to output to the gantry information relating to to a scan of a body located on a table, the X-ray CT system comprising:
a first direction unit that is mounted on the gantry and directs the gantry to move;
a second direction unit that is mounted on the operating console and directs the gantry to move;
a storage unit that stores information of a maximum range in which the gantry is moved by the first direction unit;
a control unit that controls the movable range of the gantry by the second direction unit in accordance with the maximum range in which the gantry is moved by the first direction unit; and
a deletion unit configured to delete the maximum range when a predetermined operation is performed on the table.

12. The X-ray CT system of claim 11, wherein the deletion unit is configured to delete the information stored in the storage unit in accordance with a predetermined operation in the gantry or a predetermined operation in the operating console.

13. The X-ray CT system of claim 11, wherein the pre-determined operation includes moving the table.

* * * * *

UNITED STATES PATENT AND TRADEMARK OFFICE
CERTIFICATE OF CORRECTION

| | |
|---|---|
| PATENT NO. | : 6,840,673 B2 |
| APPLICATION NO. | : 10/284671 |
| DATED | : January 11, 2005 |
| INVENTOR(S) | : Moritake et al. |

It is certified that error appears in the above-identified patent and that said Letters Patent is hereby corrected as shown below:

In Claim 3, column 11, line 14, after "encoder" delete "for".

In Claim 3, column 11, line 15, after "position in" delete "the" and insert therefor -- a --.

In Claim 4, column 11, line 22, after "linear scale" insert -- arranged --.

In Claim 5, column 11, line 27, delete "the direction" and insert therefor -- a direction --.

In Claim 11, column 12, line 41, after "relating" delete "to".

Signed and Sealed this

Twenty-third Day of January, 2007

JON W. DUDAS
*Director of the United States Patent and Trademark Office*